United States Patent [19]
Cheswick

[11] Patent Number: 5,392,509
[45] Date of Patent: Feb. 28, 1995

[54] APPARATUS FOR CAPPING USED OR UNSANITARY NEEDLES

[75] Inventor: Alfred J. Cheswick, Loch Arbour, N.J.

[73] Assignee: Krell Technologies, Inc., Loch Arbour, N.J.

[21] Appl. No.: 98,850

[22] Filed: Jul. 29, 1993

[51] Int. Cl.⁶ .............................................. B23Q 7/10
[52] U.S. Cl. ...................................... 29/818; 29/282; 29/283.5
[58] Field of Search ............... 29/422, 517, 818, 282, 29/283.5, 753; 53/484, 467, 284.5

[56] References Cited

U.S. PATENT DOCUMENTS

| | | | |
|---|---|---|---|
| 1,507,916 | 9/1924 | Granat | 29/818 |
| 3,451,116 | 6/1969 | Shields . | |
| 3,599,472 | 8/1971 | Koletsos | 29/818 |
| 3,664,173 | 5/1972 | Haucke et al. | 29/818 |
| 4,178,679 | 12/1979 | Lichtenstein | 29/753 |
| 4,332,323 | 6/1982 | Reenstierna . | |
| 4,623,336 | 11/1986 | Pedicano et al. . | |
| 4,728,320 | 3/1988 | Chen . | |
| 4,835,855 | 6/1989 | Eaton et al. | 29/753 |
| 4,852,241 | 8/1989 | Belaidouni et al. | 29/818 |
| 4,929,241 | 5/1990 | Kulli . | |
| 5,067,949 | 11/1991 | Freundlich et al. . | |
| 5,076,178 | 12/1991 | Kohl . | |
| 5,084,028 | 1/1992 | Kennedy et al. . | |
| 5,135,507 | 8/1992 | Haber et al. . | |
| 5,171,229 | 12/1992 | McNeil et al. . | |
| 5,207,653 | 5/1993 | Janjua et al. . | |

Primary Examiner—Mark Rosenbaum
Assistant Examiner—David P. Bryant
Attorney, Agent, or Firm—Sudhir G. Deshmukh; Gerry J. Elman

[57] ABSTRACT

A method for capping or crimping an isolation cell or an isolation cap, for a safe disposal, to a sharp tip of a used or otherwise unsanitary needle of a medical device and an apparatus used therefor. By capping the tip of the used needle of the medical device, such as a disposable syringe, the isolation cell effectively eliminates the risk of infection or injury to anyone exposed to the tip of the used needle during or after its disposal. The apparatus includes a dispenser containing a plurality of the isolation cells where the dispenser positions one cell at a time into an anvil for prepositioning the isolation cell to receive a tip portion of the used needle within its interior. The used needle is then inserted through an orifice disposed on needle-alignment means, for safe and easy insertion. Once the needle is inserted within the cell positioned at the anvil, a crimping tool permanently crimps or caps the cell to the needle, after which the used needle having the cell crimped or capped thereto is extracted from the apparatus. The needle-alignment means are further provided with means for permitting smooth and easy extraction of the needle having the isolation cell crimped or capped thereon.

21 Claims, 6 Drawing Sheets

APPARATUS FOR CAPPING USED OR UNSANITARY NEEDLES

FIELD OF THE INVENTION

The present invention generally relates to a method and to devices used for safe disposal of needles of medical devices after their use, and more particularly relates to a needle-capping device that caps the tips of the used needles before they are disposed of.

BACKGROUND OF THE INVENTION

In medical facilities throughout the world, medical personnel routinely inject patients intravenously, subcutaneously or intramuscularly with various fluids, such as saline or medications. Typically they use disposable injecting devices, such as syringes, catheters, or any other suitable devices, which have needles with sharp tips. The needles of these medical devices, also known in the industry as "sharps", are inserted during their use through the patient's skin. As a result, the needles are exposed to the patient's body fluids, such as blood.

Due to privacy laws as well as due to staggering number of times these needle insertions or injections are carried out throughout the world, a patient's medical history may not be readily available to medical personnel prior to administering these injections. Thus, infections from contact with unsanitary or otherwise infected needles have long posed danger to medical personnel handling such equipment. Furthermore, accidental or inadvertent contact with sharp tips of used needles or cannulae is particularly hazardous when medical personnel are involved in handling needles contaminated with blood or body fluids infected with Human Immunodeficiency Virus (HIV), or any other highly infectious agents, such as harmful bacteria, herpes virus, hepatitis virus, and the like.

Several methods and devices have been disclosed for protection from infected needles. For example, Kennedy et al. in the U.S. Pat. No. 5,084,028 disclose a dispenser for dispensing a needle cover provided with gripping surfaces for securing a used syringe body after its insertion in the needle cover.

McNeil et al. in the U.S. Pat. No. 5,171,229 disclose a dispenser containing a plurality of two-piece covers, which consist of a shaft and a metal piece bent back on itself.

Kulli in the U.S. Pat. No. 4,929,241 provides a protective guard that rides on the shaft of a needle and is slid forward after the use of the needle.

Janjua et al. in the U.S. Pat. No. 5,207,653 disclose a disposable needle having a pivotable top attached to the needle hub.

Pedicano et al. in the U.S. Pat. No. 4,623,336 disclose a one-piece disposable needle sheath having a cone-shaped opening for ease of insertion of a used needle still attached to the syringe into the sheath and retaining means that grip the used needle during the detachment of the syringe attached to the used needle. The cone-shaped opening may be provided with a top to fully enclose the used needle.

Reenstierna in the U.S. Pat. No. 4,332,323 discloses two closed-ended, coaxially-positioned, elongated members where a pliable outer member includes a plurality of rigid projections that are aligned with openings on an inner member that houses the needle. After the use, the needle is reinserted into the inner member and the outer member is hit against a dense object, such as a table, whereby the projections on the outer pliable member push through the openings on the inner member to either bend or break the needle disposed therein.

Chen in the U.S. Pat. No. 4,728,320 discloses a syringe assembly having the needle mounted inside a needle top provided with a hammer body at the end. The user reinserts the needle after its use in the needle top, which is then hit against an object to bend the needle point.

Kohl et al. in the U.S. Pat. No. 5,076,178 disclose a device that destroys a used needle by first deforming to seal and then burning the needle by the passage of an electrical current through the needle.

Freundlich et al. in the U.S. Pat. No. 4,728,320 disclose a one-piece unsheathing and resheathing device into which a syringe having a conventional sheath thereon, is inserted through a conical opening for ease of insertion. A pivotable cam is actuated to hold the sheath while the syringe having a needle thereon, is removed and used. The used needle is then reinserted into the sheath still held in the device and the pivotable cam is then reactuated to release the sheath, so that the re sheathed syringe can be safely removed.

Finally, Haber et al. in the U.S. Pat. No. 5,135,507 disclose a one-piece syringe system in which, after its use, a hinged frame containing the syringe is pivoted back upon itself and latched together to capture the needle between the front and the back part of the frame.

However, there exists a need for a needle-capping device, which is suited for capping needles of various sizes, and which is environmentally safe and easy to use.

STATEMENT OF THE INVENTION

Therefore, it is an object of the invention to provide means for an environmentally safe disposal of medical needles after their use, such that these needles, if infected with an infectious agent, such as HIV, do not pose a danger to the general public, for example, at a public beach, where one walking on the beach is not accidentally pricked and thereby infected by an unsanitary needle that may have washed ashore from an illegally dumped medical waste.

It is an object of the present invention to provide means for an environmentally safe disposal of medical needles after their use by health care workers associated with human or animal health care.

An advantage of the invention is to provide a safe needle-capping device that prevents the accidental exposure of a user's fingers or other body parts from being pricked by an infected needle during or after its disposal.

Still another advantage of the present invention is to eliminate the risk of infection or injury to someone from used or otherwise discarded needles, for example, to a child who finds a contaminated needle in the trash and pricks himself or herself while playing with the discarded needle.

It is an advantage of the present invention to provide means for an environmentally safe disposal of needles after their use by undertakers involved in the embalming process.

It is an advantage of the present invention to provide means for preventing accidental reuse of a used needle of a medical device.

It is further an advantage of the present invention to provide a portable needle-capping device that is easy to operate.

It is still another advantage of the invention to provide a needle-capping device that is inexpensive to manufacture and cost effective to operate.

It is further an advantage of the invention to render used needles or otherwise discarded needles non-usable by someone, such as a drug user.

It is further an advantage of the present invention to provide a portable needle-capping device that is easy to operate in a horizontal, vertical or inclined orientation.

The present invention is directed to a needle-capping apparatus for a safe disposal of a used or otherwise unsanitary needle of a medical device comprising a base structure, needle-alignment means disposed on the base structure, the alignment means having an orifice for inserting the needle of the medical device therethrough, positioning means disposed on the base structure and adapted to preposition an isolation cell thereon, the positioning means being aligned in an operating relationship with the needle-alignment means to allow placement of a tip of the needle inside the isolation cell, anvil means disposed on the base structure and aligned in an operating relationship with the positioning means to allow placement of a portion of the isolation cell having the tip of the needle therein, and crimping means positioned on the base structure and aligned with the anvil means and the positioning means for permanently affixing the isolation cell to the tip of the needle.

The present invention is also directed to a method of permanently capping a needle for a safe disposal of a used or otherwise unsanitary needle of a medical device comprising, inserting the needle through an orifice of needle-alignment means of a needle-capping apparatus into a cell prepositioned in positioning means of the apparatus aligned in an operating relationship with the needle-alignment means, positioning a portion of the cell having the needle positioned therein to anvil means of the apparatus, and crimping the cell to the needle to permanently affix the cell to the needle.

The present invention is also directed to a permanently capped needle of a medical device comprising, a single-piece hollow elongated member having a closed end and an open end, a portion of the needle which includes a tip of the needle positioned within the hollow member such that the tip of the needle is entirely included within the hollow member, a deformed portion proximately located near the closed end of the member having a deformed portion of the needle sandwiched therewithin.

Other advantages of the invention will become apparent upon reading the following detailed description and appended claims, and upon reference to the accompanying drawings.

BRIEF DESCRIPTION OF THE DRAWINGS

For a more complete understanding of this invention reference should now be had to the embodiments illustrated in greater detail in the accompanying drawings and described below by way of examples of the invention.

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

DETAILED DESCRIPTION OF THE PREFERRED EMBODIMENT

It should be noted that, for the sake of clarity, the same components are referred by the same Arabic numerals throughout all the Figures referred herein.

Referring now to FIGS. 1–15 there is shown a needle-capping apparatus, referred by an Arabic numeral 1, for a safe disposal of a used, dirty or otherwise unsanitary needle, such as a needle 3 shown in FIGS. 11 B, 11 C and 11 D, of a medical device, which is preferably a disposable syringe, not shown. The present method and apparatus is equally suitable for other medical devices, such as a catheter needle; a sharp pin used for pricking a finger or a suitable body portion, during blood assay test. Apparatus 1, by crimping, capping or otherwise permanently affixing an isolation cell or cap 4 to a sharp tip 5, shown in FIGS. 11 B and 11 C, of needle 3, provides protection to a user from accidental or inadvertent infection or injury by sharp tip 5 of needle 3. Sharp tip 5 for the purposes of the present invention includes a length portion of needle 3 sufficient in length to substantially permanently affix isolation cell 4 to needle 3. Such a length, preferably, would be about a third to about the entire length of needle 3.

Figure 11A:
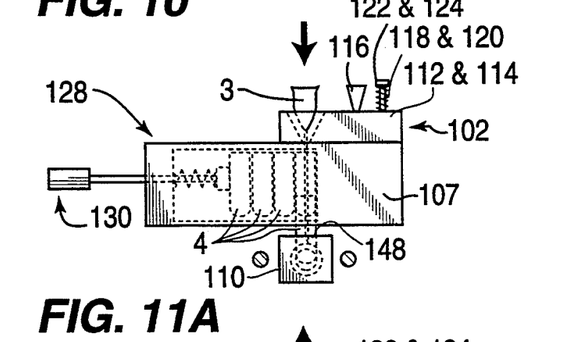
Figure 11B:
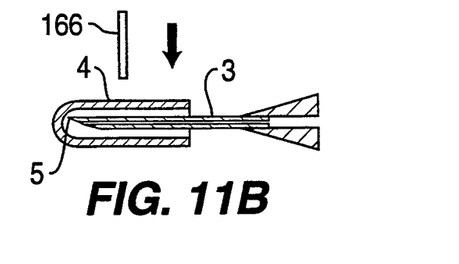
FIGS. 11B–11D are partial cross sectional sequential details of the needle and the cell, shown in FIGS. 9, 10, 11A, 12 and 13.
Figure 11C:
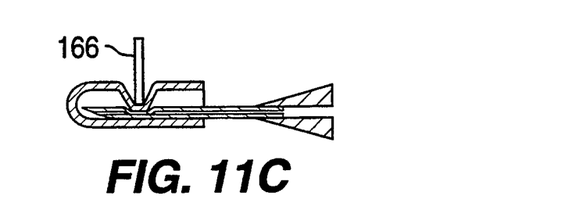
Figure 11D:
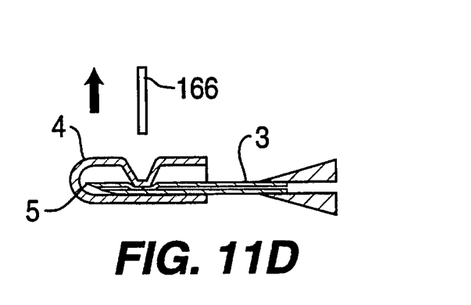
Figure 12:
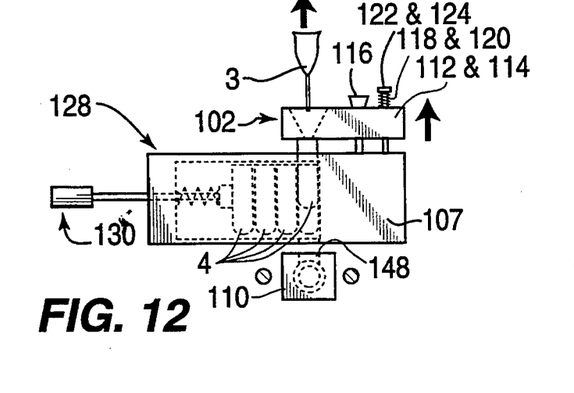
Figure 13:
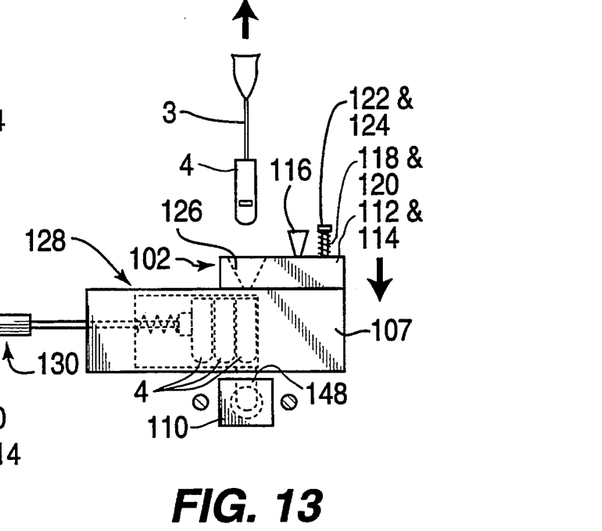

Isolation cell 4 is provided with a shape that permits isolation of tip 5 of needle 3 by placement of needle 3 including tip 5 within cell 4 and cell is made from a deformable material that is substantially corrosion resistant. Suitable materials are stainless steel, nickel plated steel, copper, aluminum brass or any surface treated versions thereof. Depending on the type of material selected for isolation cell 4, some of the suitable surface treatments are plating, anodizing, painting, coating and oxidizing. Copper is preferred. Isolation cell 4, as shown in FIGS. 11 B, C and 11 D, is preferably a hollow, elongated member closed at one end and open at the other end. The closed end may be provided with a bullet shape, flat-end shape or a conical shape. Bullet shape is preferred. Isolation cell 4 is preferably cylindrical in shape having an inner diameter at least 10 percent larger than the outer diameter of needle 3 and having a length of about 20 percent to about 90 percent of the length of needle 3. Isolation cell 4 having a cylindrical shape with an outer diameter of about 0.084 to about 0.25 inches, a wall thickness of about 0.003 to about 0.02 inches, and a length of about 0.2 to about 2 inches is most preferred.

Apparatus 1 is provided with a base structure 100 made of light weight material, such as aluminum or polymer plastics, such as polycarbonate, for providing base structure 100 with portability. Polymer plastics is preferred. Base structure 100 is preferably substantially planar. One skilled in the art would preferably provide base structure 100, with means, such as handles (not shown), to improve portability of apparatus 1. Apparatus 1 is further provided with needle-alignment means, which are disposed on base structure 100 and are indicated by a numeral 102.

An orifice 104 is disposed on needle-alignment means 102 for allowing insertion of needle 3 therethrough. Orifice 104 is further provided with needle-guiding means, such as a cone-shaped opening 126 having orifice 104 at its apex. Cone-shaped opening 126 aids the user in guiding needle 3 into orifice 104. Orifice 104 is preferably circular in shape, having a diameter greater than at least about 10 percent of the outer diameter of needle 3. Furthermore, the inner diameter of cell 4 is greater than at least about 10 percent of the diameter of orifice 104. Orifice 104 having a diameter of about 0.065 to 0.070 is most preferred.

Figure 1:
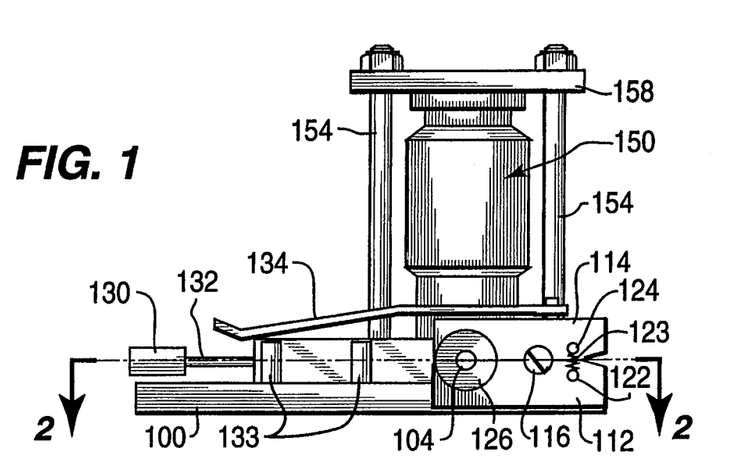
FIG. 1 is an elevational view of a preferred embodiment of the invention.
Figure 1A:
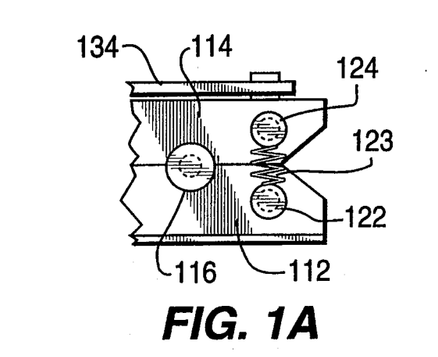
FIG. 1A is a partial view of the embodiment of FIG. 1.
Figure 5:
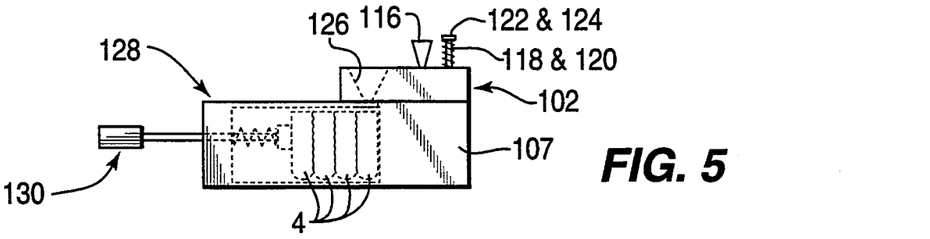
FIG. 5 is a partial plan view of the dispensing means of FIG. 3 connected to positioning and needle-alignment means of the embodiment of FIG. 1 where the needle-alignment means are in a closed position.
Figure 6:
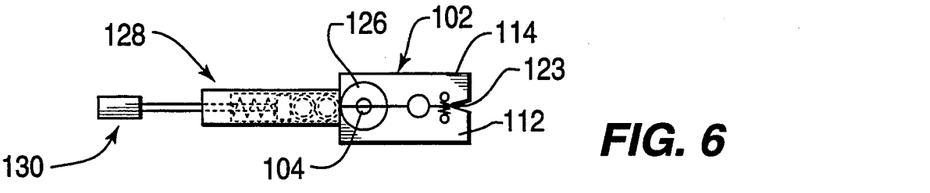
FIG. 6 is a partial side view of FIG. 5.
Figure 7:
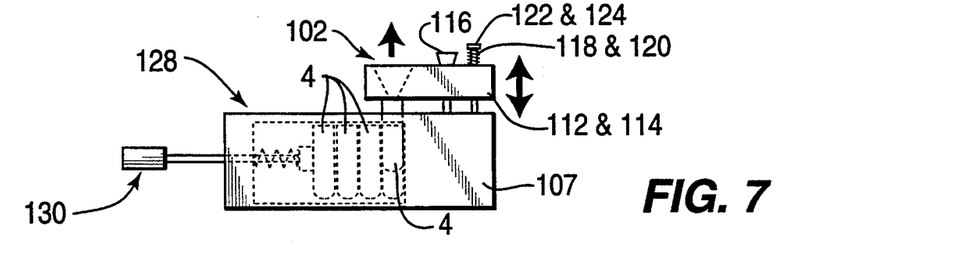
FIG. 7 is a partial plan view of the dispensing means of FIG. 3 connected to positioning and needle-alignment means of the embodiment of FIG. 1 where the needle-alignment means are separated from each other.
Figure 8:
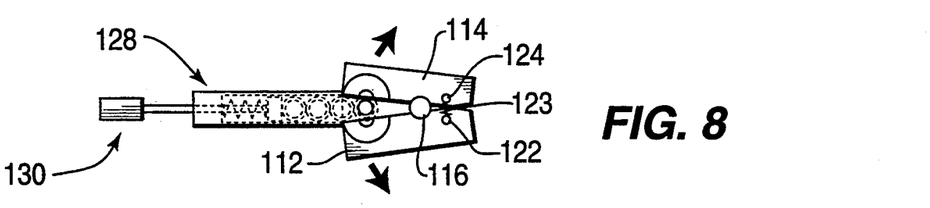
FIG. 8 is a partial side view of FIG. 7.
Figure 9:
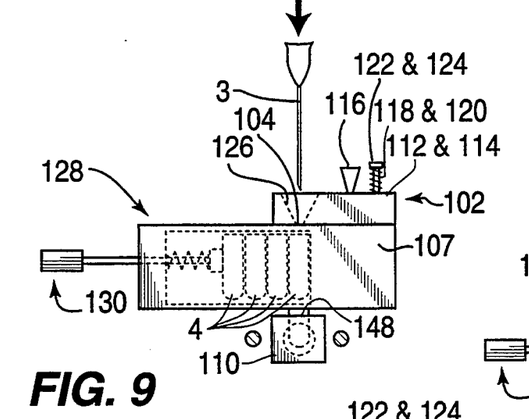
FIGS. 9, 10, 11A, 12 and 13 are sequential views of dispensing means of FIG. 3 connected to positioning, anvil and needle-alignment means of the embodiment of FIG. 1 illustrating a crimping of a needle with a cell.

Needle-alignment means 102 further comprise an upper cam rider half 112 and a lower cam rider half 114, each of which is adapted to separate, as shown in FIGS. 7 and 8, from each other during extraction from apparatus 1 of needle 3 having isolation cell 4 affixed thereto. As shown in FIG. 1, substantially half of orifice 104 is disposed on each of cam rider halves 112 and 114. A pair of cam rider halves 112 and 114 are preferably made of a substantially elongated member, such as a rectangular bar, of a material that may not be easily scoured, scratched or otherwise significantly damaged by sharp tip 5. Suitable materials are stainless steel, toughened zirconia ceramic disclosed on page 2571 (Part Number 8750K131) in McMaster-Carr Supply Company (Dayton, N.J.) Catalog Number 99 (1993 Edition), or high carbon steels. Stainless steel is preferred. As shown in FIG. 1, cam rider halves 112 and 114 are provided with substantially half of orifice 104 at one end and a pivot point 122 and 124, respectively, at other end, such that when cam rider halves 112 and 114 are pressed together, as shown in FIGS. 5 and 6, each half of orifice 104, disposed on each cam rider halves 112 and 114, respectively, contacts with one another to form a completed orifice 104 shown in FIGS. 1 and 6. As shown in FIGS. 1-8, a pivot hole on each of the other end of cam rider half 112 and cam rider half 114 is slidably and rotatably mounted on a first pivot post 122 and a second pivot post 124, respectively, such that cam rider halves 112 and 114 can slide in the direction of arrows, as shown in FIG. 7, as well as rotate, as shown in FIG. 8, on first and second pivot post 122 and 124, respectively. If desired, lubrication, such as a silicone lubricant, may be applied to first and second pivot posts 122 and 124 for reducing sliding and rotational friction. Needle alignment biasing means, preferably a first compression spring 118 and a second compression spring 120 are mounted on first pivot post 122 and second pivot post 124, respectively, to keep cam rider halves 112 and 114 close to each other while needle 3 is inserted through orifice 104.

Figure 2:
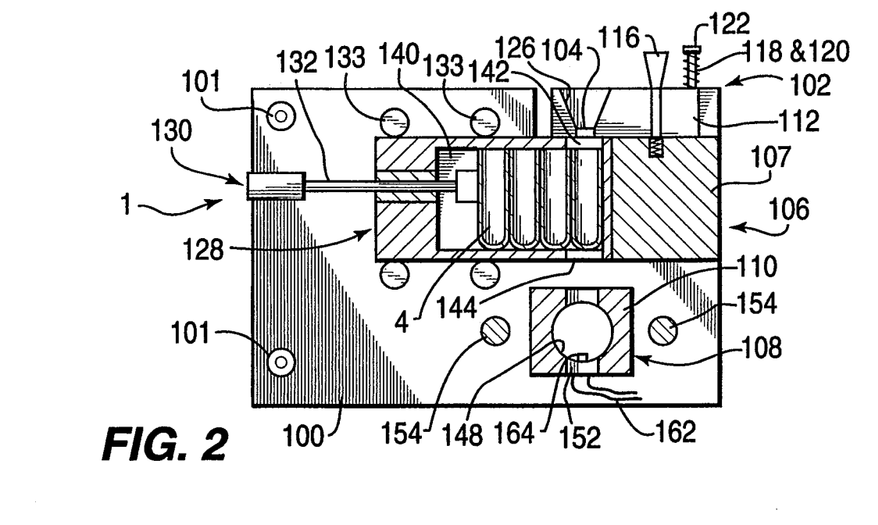
FIG. 2 is a cross sectional plan view taken along a cross section 2—2 of FIG. 1 of the embodiment of FIG. 1.

As stated earlier and as shown in FIGS. 7 and 8, cam rider halves 112 and 114 of needle-alignment means 102 are also adapted to separate from each other to allow smooth and effortless extraction of needle 3 having cell 4 affixed thereto. Separating means, such as a cam 116, preferably having an inverted cone shape, separate cam rider halves 112 and 114 as they slide over the surface of cam 116 during extraction from apparatus 1 of needle 3 having cell 4 affixed thereto. Cam 116 is preferably made from a hardened material, such as stainless steel, having a smooth surface over which cam rider halves 112 and 114 slide. If desired, a lubricating material, such as a silicone lubricant, may be provided to reduce friction along the surface of cam 116. As shown in FIGS. 2, 6 and 8, needle alignment tension means, preferably a first tension spring 123, is mounted over first pivot post 122 and second pivot post 124 to bring cam rider halves 112 and 114 close to each other after extraction of needle 3 having isolation cell 4 affixed thereto. First tension spring 123, as compared to the pull provided by the user during extraction of needle 3 from apparatus 1, exerts significantly less force on cam rider halves 112 and 114, such that the user does not find any difficulty or hindrance in extracting needle 3 having isolation cell 4 affixed thereto from apparatus 1.

Apparatus 1 is further provided with positioning means 106 disposed on base structure 100 and aligned in an operating relationship with needle-alignment means 102 to allow placement of tip 5 of needle 3, as shown in FIGS. 11 B, 11 C and 11 D, inside isolation cell 4. Positioning means 106 prepositions isolation cell 4 in apparatus 1 before needle 3 is inserted through orifice 104 into apparatus 1. Positioning means 106 comprise a positioning block 107 fastened to base structure 100 by a threaded or a welded joint and dispenser means 128, which are detachably engaged to positioning block 107. Positioning block 107 is preferably an integral part of base structure 100, which is preferably produced by conventional fabrication processes, such as injection molding.

Figure 3:
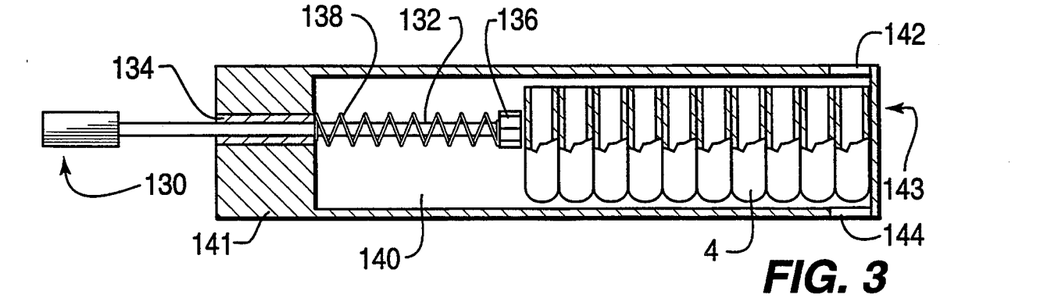
FIG. 3 is a partial cross sectional plan view taken along a cross section 2—2 of FIG. 1 of dispensing means used in the embodiment of FIG. 1.
Figure 4:
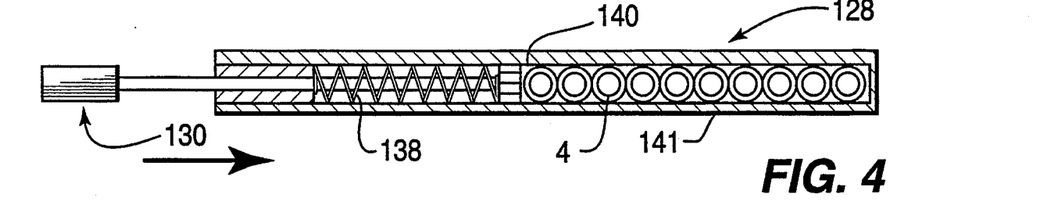
FIG. 4 is a partial cross sectional side view of the dispensing means of FIG. 3.

Positioning block 107 is further provided with clip means, such as a clamp 134, to readily engage or disengage dispenser means 128 to positioning block 107. Alignment means, such as pins 133 are positioned on base structure 100 to align dispenser means 128 with respect to positioning block 107. Dispenser means 128 comprise, as shown in FIGS. 3 and 4, a cavity 140 adapted to store a plurality of isolation cells 4 arrayed to allow the placement of tip 5 of needle 3 therein. Dispenser means 128 are further provided with isolation cell biasing means 130 to urge the plurality of isolation cells 4 stored in cavity 140 towards aperture means 143 located on dispenser means 128 and situated near positioning block 107. Aperture means 143 located on dispenser means 128 comprise a first aperture 142 and a second aperture 144, where first aperture 142 and second aperture 144 are aligned with orifice 104 to allow passage of needle 3 therethrough. The size of first aperture 142 and second aperture 144 is sufficiently larger than outer dimensions of isolation cell 4 to allow smooth and easy passage of isolation cell 4 through them.

Dispenser means 128 are provided with isolation cell biasing means 130, which preferably comprise, as shown in FIGS. 3 and 4, a compression spring 138 mounted on a push rod 132 passing through a bushing 134 positioned at one extremity of dispenser means 128. A push rod end 136, preferably shaped to improve engagement with isolation cells 4 stored in cavity 140, urges isolation cells 4 towards the aperture means located on dispenser means 128. Cavity 140 is formed within an enclosure 141. When cavity 140 is filled with isolation cells 4, compression spring 138 gets compressed and thereby provides the force necessary to urge isolation cells towards the aperture means located on dispenser means 128. It is contemplated that dispenser means 128, filled with a plurality of isolation cells 4, are preferably a disposable item purchased by the user and enclosure 141 is made of stainless steel, aluminum, brass, plated steel or preferably injection molded polymer material, such as acrylonitryl butadiene styrene (ABS), polycarbonate, polystyrene, polyvinyl chloride.

Apparatus 1 is further provided with anvil means 108 disposed on base structure 100 and aligned in an operating relationship with needle-alignment means 102 and positioning means 106 to allow placement of tip 5 of needle 3 inside isolation cell 4. Anvil means 108 comprise an anvil block 110 aligned and preferably shaped to allow the placement of a portion, i.e., the closed end portion, of isolation cell 4 having tip 5 of needle 3 placed therein through anvil aperture 148 aligned with second aperture 144 of aperture means 143.

Figure 2A:
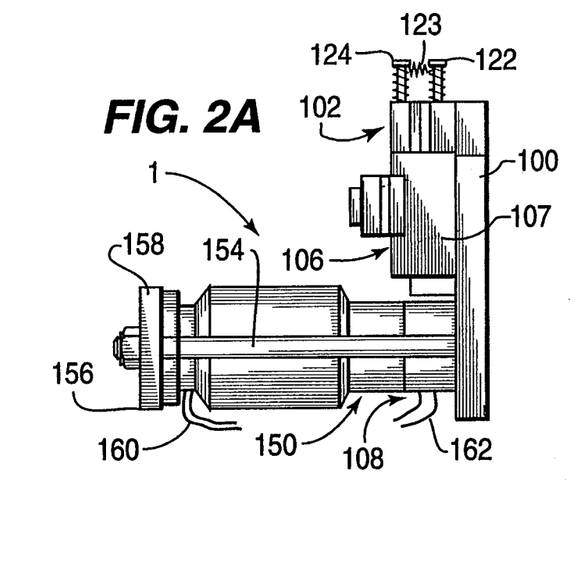
FIG. 2A is a side elevational view of the embodiment of FIG. 1.
Figure 14:
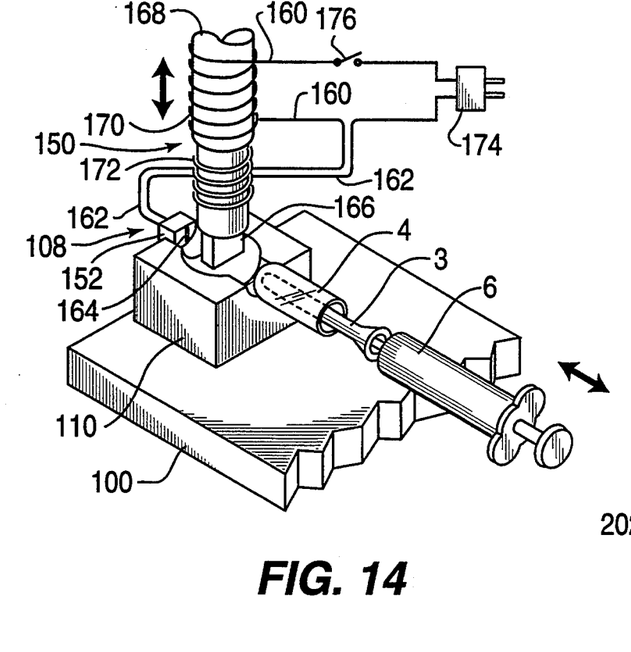
FIG. 14 is an exploded partial isometric view of crimping means of the embodiment of FIG. 1.

Apparatus 1 is further provided with crimping means 150, shown in FIGS. 1, 2A and 14, disposed on base structure 100 and aligned in an operating relationship with needle-alignment means 102 and positioning means 106, to permanently affix tip 5 of needle 3 to isolation cell 4 by manually, electromechanically or pneumatically crimping or bonding tip 5 of needle 3 to isolation cell 4. The aforementioned "crimping or bonding" term is defined as permanent affixing of cell 4 to needle 3 by physical deformation of cell 4 and needle 3 as shown in FIG. 11C. Electromechanically operated crimping means are preferred.

Crimping means 150 are aligned and affixed on top of anvil block 110 of anvil means 108 by connecting means, such as bolts 154, threaded into base structure 100 and retainer plate 158 located on top of crimping means 150. As shown in FIG. 14 (shown with needle-alignment means 102, positioning means 106 and dispenser means 128 removed for better understanding), crimping means 150, shown with its housing removed, comprise a conventional solenoid device formed by an induction coil 170, preferably made of copper, having a solenoid core 168, preferably of iron, connected to hammer means 166 engaged in an operational relationship with anvil means 108 and slidably positioned in coil 170. Core 168 normally rests on top of a core return compression spring 172, which keeps core 168 in a hammer "up" position. An electrical circuit for energizing coil 170 comprises electrical connectors 160, such as electrical wires, for supplying electrical power to coil 170, electrical power connecting means, such as an electrical plug 174 and a triggering switch 152, positioned in anvil block 110 and connected by electrical conductors 162 for triggering crimping means 150. The electrical power suitable for use in the present invention may be supplied from an alternating current (AC) power source, such as a standard 115 or 220 Volt, 60 or 50 Hertz power supply or from a direct current (DC) power source, such as from a portable battery. Preferably, a conventional "ON/OFF" switch 176 is also included in the electrical circuit to improve the operator safety. Triggering switch 152 can be any of the conventional switches, such as a micro switch, a proximity switch, which triggers in the presence of any changes in a magnetic field or a dielectric field around anvil means 108, or a light sensor switch triggered by the interruption of a beam of light by cell 4 passing through the beam. A conventional micro switch, such as a pin plunger actuated precision snap-acting switch described on page A-6 of the catalog No. 49003 of C & K/Unimax, Inc., Wallingford, Conn., is preferred. Hammer means 166 comprise a replaceable blade of toughened zirconia ceramic disclosed on page 2571 (Part Number 8750K131) in McMaster-Carr Supply Company (Dayton, N.J.) Catalog Number 99 (1993 Edition), or preferably tool steel hardened to Rockwell hardness of about 50 to 55 in "C" scale for long wear life.

Figure 15A:
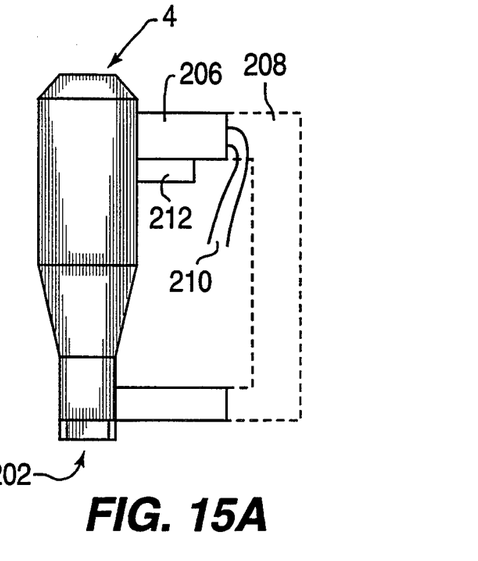
FIG. 15A is a partial side view showing modifications made to a conventional stapler to adapt the stapler for use in the embodiment of FIG. 1.
Figures 15B, 16:
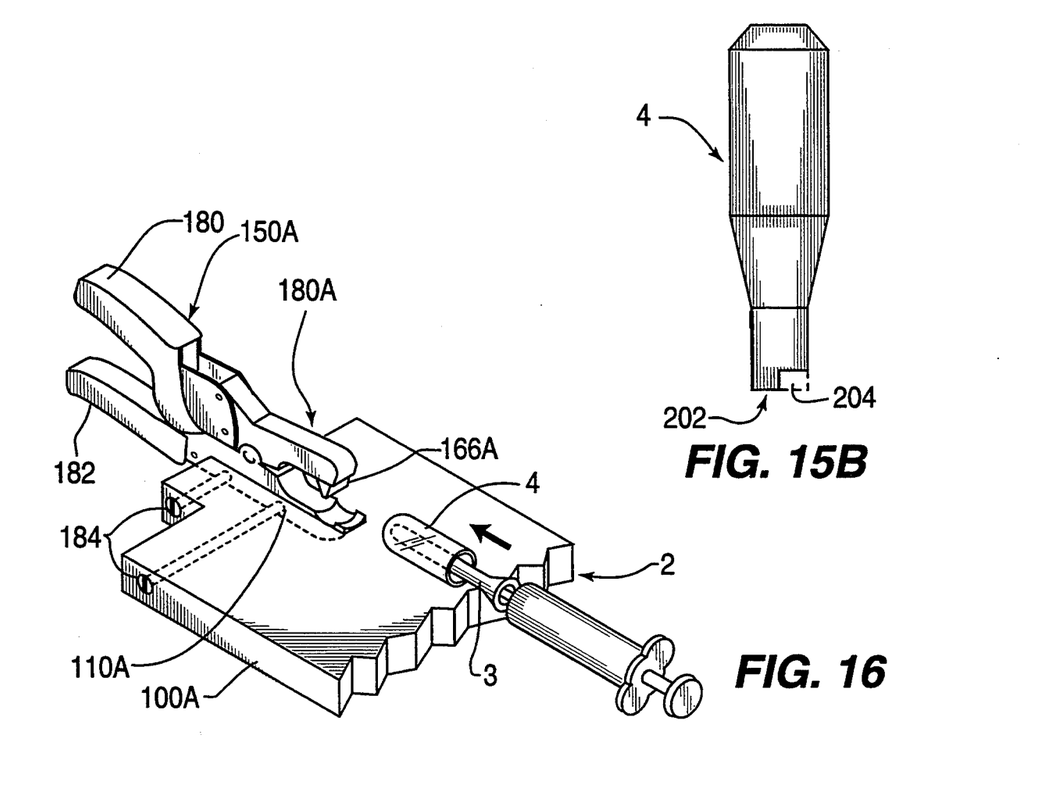
FIG. 15B is a partial front view of FIG. 15A.
FIG. 16 is an exploded partial isometric view of crimping means of another embodiment of the invention.

The aforedescribed conventional solenoid device of crimping means 150, most suitable for use in the present invention, is supplied by Stanley-Parker, Inc., Worcester, Mass. having a model number TRE50, which is used as a stapler. The TRE50 stapler 4, as shown in FIGS. 15A and 15B, is modified for use in the present invention by removing a portion 204, shown as a dotted line in FIG. 15B, to reshape a stapler end 202 on top of anvil means 110, modifying a stapler solenoid housing 206 by removing a handle portion 208, shown as a dotted line in FIG. 15A, to fit in apparatus 1, and disconnecting electrical leads 210 connected to stapler hand trigger switch 212 and reconnecting leads 208, which then become electrical conductors 162 to triggering switch 152. It is understood, that instead of modifying an existing stapler 4 of FIG. 15, one skilled in the art would provide a housing specifically made for crimping means 150 of apparatus 1.

Figure 10:
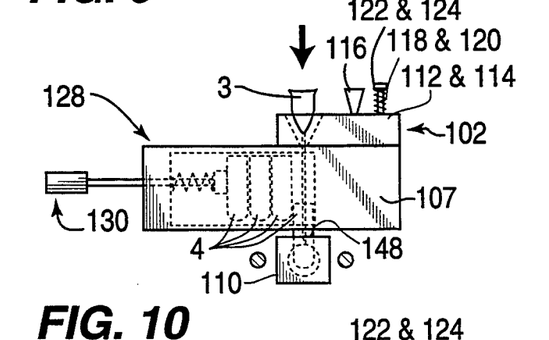

In operation, as shown sequentially in FIGS. 9–13, the operator commences insertion of needle 3 through orifice 104 of needle-alignment means 102, then through aperture means 143 of dispenser means 128 into cell 4. As the needle-insertion continues, a portion of cell 4 having needle 3 therein (as shown in FIG. 10) is pushed through second aperture 144 of aperture means 143 and anvil aperture 148 of anvil means 108. As shown in FIG. 11A, cell 4 continues to push through anvil aperture 148 of anvil means 108 to finally contact trigger point 164 of triggering switch 152. As a result, a signal generated by triggering switch 152 energizes solenoid 170, thereby resulting in crimping of cell 4, as shown in FIG. 11C, by hammer means 166. Once crimping is completed, return spring 172 pushes crimping means 150 into the hammer "UP" position. The operator thereafter retracts needle 3 having cell 4 affixed thereon. As the retraction continues, cell 4 contacts and then pushes cam rider halves 112 and 114 in the direction of arrows shown in FIG. 12. As a result, cam rider halves 112 and 114 slide over cam 116 and separate from one another by rotating on first pivot post 122 and second pivot post 124, respectively and thereby creating, as shown in FIG. 8, a gap between cam rider halves 112 and 114 through which cell 4 as it is being retracted by the operator can easily pass through. Once needle 3 having cell 4 affixed thereto, clears needle-alignment means 102, first tension spring 123 brings cam rider halves back together and push rod 132 pushes and aligns the next cell 4 with first aperture 142 and second aperture 144 of aperture means 143 of dispenser means 128. The cycle can then be repeated.

In another embodiment of the present invention, apparatus 2 of FIG. 16 (shown with needle-alignment means 102, positioning means 106, and dispenser means 128 removed for better understanding), there is shown a base structure 100A having manually operated crimping means 150A affixed thereon. Manual crimping means 150A are provided with handles 182 and 180 and anvil means 108A formed by a fixed jaw and a movable jaw having hammer means 166A positioned thereon. The fixed jaw of manual crimping means 150A is permanently secured to base structure 100A by threaded means, such as screws 184. Manual crimping means 150A most suitable for use with the present invention is supplied by Paladin®, as described on page 552 of Allied Electronics No. 3910 Engineering Manual and Purchasing Guide and known as Econocrimp ™ having catalog number 889-1330 and Model number PA-1330 or catalog number 889-1331 and Model number PA-1331 or by Amp Industries, Harrisburg, Pa., as described on page 193 of the aforementioned Manual and known as "Commercial Dual Crimp Tool-Ratcheted" having a catalog number 512-2224 and Manufacturer's number 220190-1 or having a catalog number 512-2226 and Manufacturer's number 220189-3.

As stated in the operational sequence earlier, once cell 4 having needle 3 therein, is positioned under hammer means 166A, the operator squeezes handles 180 and 182 to crimp cell 4 to needle 3. The movable jaw and the fixed jaw of manual crimping means 150A are adapted to complete the crimping cycle, once the operator commences the squeezing of handles 180 and 182, i.e., the movable jaw of manual crimping means 150A. Once the crimping step commences, handles 180 and 182 cannot be retracted back until completion of the crimping cycle. As a result partial or incomplete crimping of cell 4 to needle 3 is avoided and a secure bonding between cell 4 and needle 3 is insured.

In another embodiment of the present invention, apparatus 7 of FIGS. 17–20, there is shown a base structure 100B having another embodiment of needle-alignment means 102A. The remaining elements of apparatus 7 are the same as those in apparatus 1 and therefore, such common elements are represented by the same Arabic numerals.

An orifice 104A, which is similar to orifice 104 of apparatus 1, shown in FIG. 1, is disposed on needle-alignment means 102A for allowing insertion of needle 3 therethrough. Orifice 104A is further provided with needle-guiding means, such as a cone-shaped opening 126A having orifice 104A at its apex. Cone-shaped opening 126A aids the user in guiding needle 3 into orifice 104A. Orifice 104A is preferably circular in shape, having a diameter greater than at least about 10 percent of the outer diameter of needle 3. Furthermore, the inner diameter of cell 4 is greater than at least about 10 percent of the diameter of orifice 104A. Orifice 104A having a diameter of about 0.065 to about 0.070 inches is most preferred.

Figures 17, 18, 19:
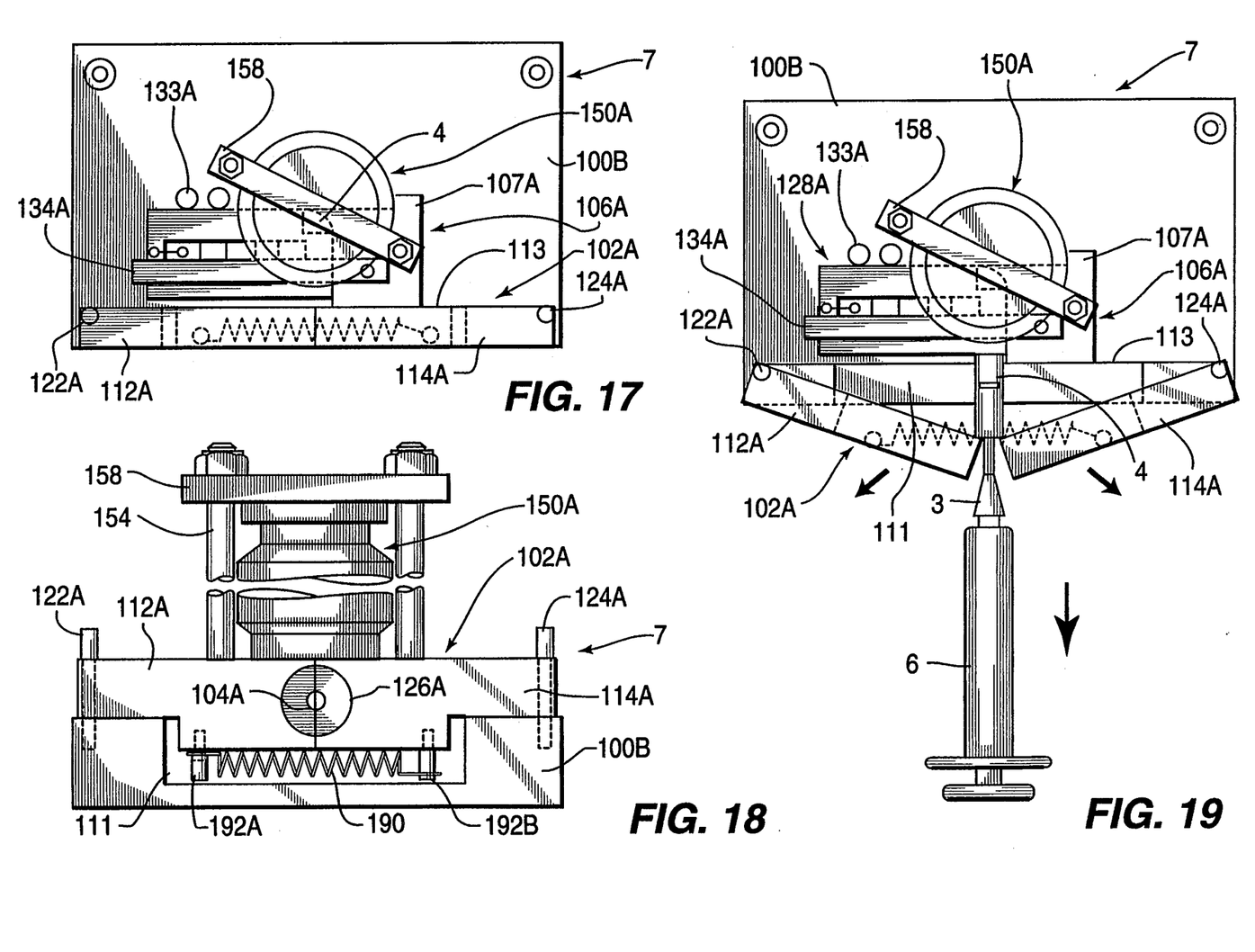
FIG. 17 is a plan view of yet another embodiment of the invention.
FIG. 18 is a partial elevational view of the embodiment of FIG. 17.
FIG. 19 is an elevational view of the embodiment of FIG. 17 with needle-alignment means of FIG. 17 separated from each other.

Needle-alignment means 102A further comprise a left side member 112A and a right side member 114A, each of which is adapted to separate, as shown in FIG. 19, from each other during extraction from apparatus 7 of needle 3 having isolation cell 4 affixed thereto.

As shown in FIG. 18, substantially half of orifice 104A is disposed on each of members 112A and 114A. Members 112A and 114A are preferably made of a substantially elongated member, such as a rectangular bar, of a material that may not be easily scoured, scratched or otherwise significantly damaged by sharp tip 5. Suitable materials are stainless steel, toughened zirconia ceramic disclosed on page 2571 (Part Number 8750K131) in McMaster-Carr Supply Company (Dayton, N.J.) Catalog Number 99 (1993 Edition), or high carbon steels. Stainless steel is preferred. As shown in FIG. 18, left side member 112A and right side member 114A are provided with substantially half of orifice 104A at one end and a pivot hole 122A and a pivot hole 124A, respectively, at other end, such that when a pair of members 112A and 114A is aligned with each other, as shown in FIGS. 17 and 18, each half of orifice 104A, disposed on each members 112A and 114A, respectively, aligns with one another to form a completed orifice 104A shown in FIG. 18. As shown in FIGS. 17–19, pivot holes 122A and 124A, respectively, on each of the other end of member 112A and member 114A is slidably and rotatably mounted on a first pivot post 122A and a second pivot post 124A, respectively, such that left side and right side members 112A and 114A, respectively, can rotate in the direction of arrows, shown in FIG. 19, on first and second pivot post 122A and 124A, respectively. If desired, lubrication, such as a silicone lubricant, may be applied to first and second pivot posts 122A and 124A for reducing sliding and rotational friction. Needle alignment biasing means, preferably a second tension spring 190, is mounted on a left side tension spring post 192A, located on left side member 112A, and a right side tension spring post 192B, located on right side member 112B, respectively, to align and keep members 112A and 114A close to each other while needle 3 is inserted through orifice 104A. First tension spring 190 is preferably positioned in a spring slot 111 provided on base structure 100B which is located below members 112A and 114A. Members 112A and 114A, as seen in FIGS. 17 and 19, also press against a vertical wall 113 on base structure 100B, which forms part of spring slot 111, while needle 3 is inserted by the user through orifice 104A, thereby ensuring linear alignment that members 112A and 114A during insertion of needle 3 through orifice 104A.

Apparatus 7 is further provided with positioning means 106A disposed on base structure 100B and aligned in an operating relationship with needle-alignment means 102A to allow placement of tip 5 of needle 3, as shown in FIGS. 11 B, 11 C and 11 D, inside isolation cell 4. Positioning means 106A prepositions isolation cell 4 in apparatus 7 before needle 3 is inserted through orifice 104A into apparatus 7. Positioning means 106A comprise a positioning block 107A fastened to base structure 100B by a threaded or a welded joint and another embodiment of dispensing means, referred by numeral 128A, which are detachably engaged to positioning block 107A. The details of dispensing means 128A are shown in FIGS. 21A-21D. Positioning block 107A is preferably an integral part of base structure 100B, which is preferably produced by conventional fabrication processes, such as injection molding.

Positioning block 107A is further provided with clip means, such as a clamp 134A, to readily engage or disengage dispenser means 128A to positioning block 107A. Alignment means, such as pins 133A are positioned on base structure 100B to align dispenser means 128A with respect to positioning block 107A.

Dispenser means 128A comprise, as shown in FIGS. 21A-21D, a cavity 140A adapted to store a plurality of isolation cells 4 arrayed to allow the placement of tip 5 of needle 3 therein. Dispenser means 128A are further provided with isolation cell biasing means 130A to urge the plurality of isolation cells 4 stored in cavity 140A towards aperture means 143A located on dispenser means 128A and situated near positioning block 107A. Aperture means 143A located on dispenser means 128A comprise a first aperture 142A and a second aperture 144A, where first aperture 142A and second aperture 144A are aligned with orifice 104A to allow passage of needle 3 therethrough. The size of first aperture 142A and second aperture 144A is sufficiently larger than outer dimensions of isolation cell 4 to allow smooth and easy passage of isolation cell 4 through them. A portion 190 near second aperture 144A is cut out to expose the closed end of cell 4, such that about 25 to about 50 percent of the length of cell 4 is exposed.

Isolation cell biasing means 130A preferably comprise, as shown in FIGS. 21A-21D, a leaf spring 138A, which is mounted on top of an enclosure 141A of dispensing means 128A. One end of leaf spring 138A is bonded or mechanically anchored to the upper face of enclosure 141A and the other end is bonded or mechanically anchored to the upper face of a biasing block 136A after passing through an advance channel 192 located on the upper face of enclosure 141A. Biasing block 136A is preferably shaped to improve engagement with isolation cells 4 stored in a cavity 140A formed within enclosure 141A. Leaf spring 138A is from a material suited to provide a constant force against isolation cells 4 stored in cavity 140A. Suitable materials for leaf spring 238A are spring steel, stainless steel or polymer material, such as Nylon ® polyamide. Stainless steel is preferred. Isolation cell biasing means 130A urges isolation cells 4 towards the aperture means located on dispenser means 128A. When cavity 140A is filled with isolation cells 4, leaf spring 138A gets compressed and thereby provides the force necessary to urge isolation cells towards the aperture means located on dispenser means 128A. It is contemplated that dispenser means 128A, filled with a plurality of isolation cells 4, are preferably a disposable item purchased by the user and enclosure 141A is made of stainless steel, aluminum, brass, plated steel or preferably injection molded polymer material, such as acrylonitryl butadiene styrene (ABS), polycarbonate, polystyrene, polyvinyl chloride. Advance channel 192 of dispenser means 128A also allows the operator to view the number of isolation cells 4 still remaining within cavity 140A. Once the operator determines that dispenser means 128A has been depleted, i.e., all isolation cells 4 have been used up, the operator can replace depleted dispenser means 128A with a new fully loaded dispenser means 128A.

Figure 20:
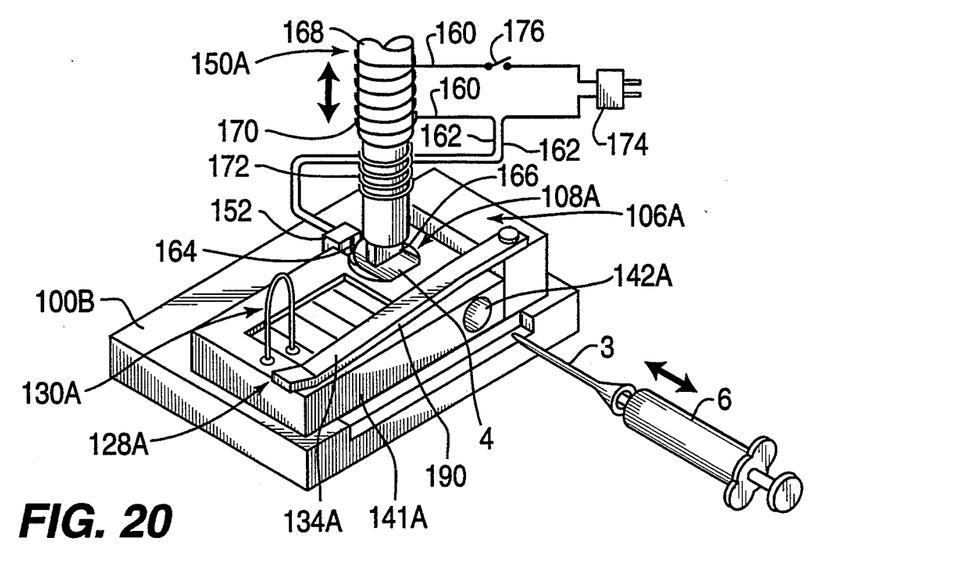
FIG. 20 is an exploded partial isometric view of crimping means of embodiment of FIG. 17.
Figure 21A:
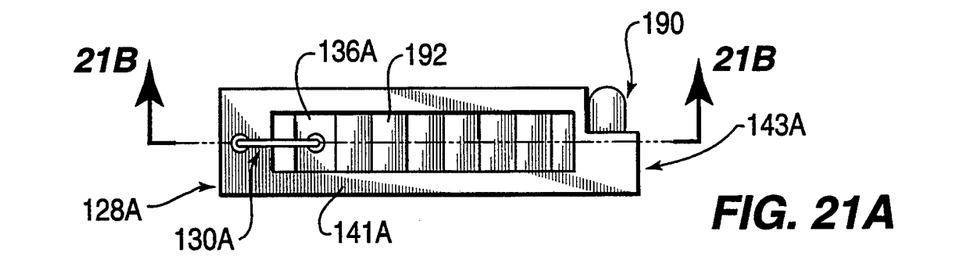
FIG. 21A is a plan view of another embodiment of dispensing means used in the embodiment of FIG. 17.
Figure 21B:
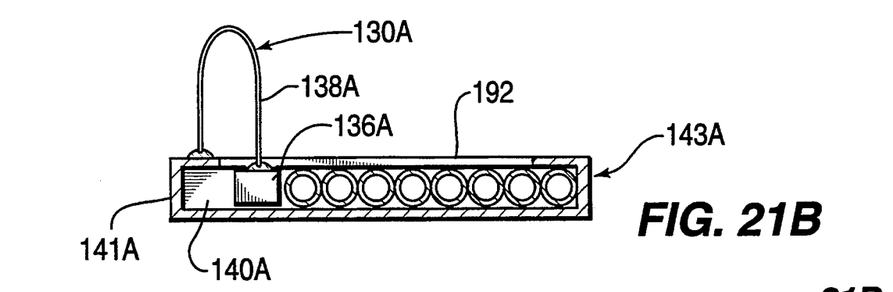
FIG. 21B is a cross sectional elevational view taken along a cross section B—B of FIG. 21A.
Figure 21C:
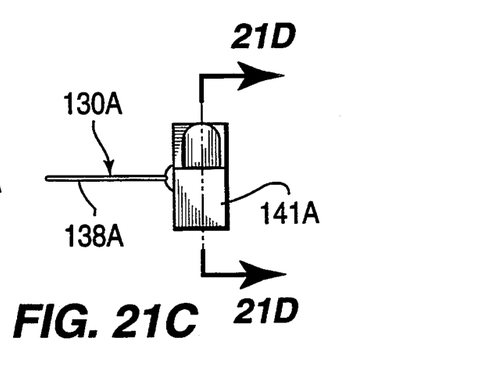
FIG. 21C is an end view of the dispensing means of FIG. 21A.
Figure 21D:
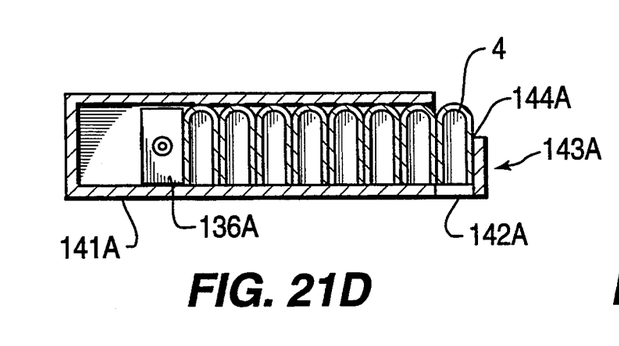
FIG. 21D is a cross sectional plan view taken along a cross section D—D of FIG. 21C.

Apparatus 7 is further provided with crimping means 150A shown in FIGS. 17-19, disposed on base structure 100B and aligned in an operating relationship with needle-alignment means 102A and positioning means 106A, to permanently affix tip 5 of needle 3 to isolation cell 4. In almost all aspects crimping means 150A are similar to crimping means 150 of apparatus 1, except its operating relationship with positioning means 106A, and anvil means 108A as shown in FIG. 20 of apparatus 7. Unlike apparatus 1, portion 190 near second aperture 144A of dispensing means 128A having the exposed portion of cell 4 therein (as seen in FIG. 21A) is positioned directly underneath hammer means 166, such that when needle 3 is inserted in apparatus 7, there is no need for the operator, unlike apparatus 1, to slide cell 4 into anvil means 108 as shown in FIGS. 9-14 of apparatus 1.

As stated earlier and as shown in FIG. 19, members 112A and 114A of needle-alignment means 102A are also adapted to separate from each other to allow smooth and effortless extraction of needle 3 having cell 4 affixed thereto. Thus when the operator, after completing the previously described crimping process, extracts needle 3 having cell 4 affixed thereto out of apparatus 3, cell 4 pushes members 112A and 114A in the direction of extraction, which thereby results in rotation of members 112A and 114A on first and second pivot posts 122A and 124A. As a result, members 112A and 114A separate from each other and allow smooth and effortlessly extraction of needle 3 having cell 4 affixed thereto out of apparatus 7. As cell 4 affixed to needle 3 is extracted out of apparatus 7, the next cell 4 then advances into position for use during a subsequent cycle.

As shown in FIGS. 11B-11D and described earlier, the present invention is also directed to needle 3 having a cell 4 affixed thereto.

While particular embodiments of the invention have been shown, it will be understood, of course, that the invention is not limited thereto since modifications may be made by those skilled in the art, particularly in light of the foregoing teachings. It is, therefore, contemplated by the appended claims to cover any such modifications as incorporating those features which constitute the essential features of these improvements within the true spirit and scope of the invention.

I claim:

1. A needle-capping apparatus for a safe disposal of a used or otherwise unsanitary needle of a medical device comprising:

a base structure;

needle-alignment means disposed on said base structure, said alignment means comprising two members, each said member having substantially half of an orifice on one end thereof for inserting said needle of said medical device therethrough, each said member being rotatively mounted on a pivot post on the other end of each said member;

positioning means disposed on said base structure and adapted to preposition an isolation cell onto said positioning means, said positioning means being aligned in an operating relationship with said needle-alignment means to allow placement of a tip of said needle inside said isolation cell;

anvil means disposed on said base structure and aligned in an operating relationship with said positioning means to allow placement of a portion of said isolation cell having said tip of said needle therein onto said anvil means; and crimping means positioned on said base structure and aligned with said anvil means and said positioning means for permanently affixing said isolation cell to said tip of said needle.

2. The apparatus of claim 1 wherein said needle-alignment means comprise:

needle alignment biasing means for keeping said members close to each other during said insertion of said needle through said orifice.

3. The apparatus of claim 1 wherein said orifice of said needle-alignment means further comprises a cone-shaped opening having said orifice located at its apex, said cone-shaped opening being substantially equally disposed on said members of said needle-alignment means.

4. The apparatus of claim 1 wherein said members of said needle-alignment means comprise:

an upper and a lower cam rider half, said cam rider halves being adapted to separate from each other during extraction from said apparatus of said needle having said isolation cell affixed thereto;

a cam interposed in a sliding relationship between said cam rider halves for separating said cam rider halves during said extraction of said needle having said isolation cell affixed thereto; and needle alignment biasing means for keeping said cam rider halves close to each other during said insertion of said needle through said orifice.

5. The apparatus of claim 4 wherein said cam is a stationary cone-shaped member.

6. The apparatus of claim 1 wherein said isolation cell is a hollow elongated member closed at one end and open at the opposite end to allow said isolation cell to receive said tip of said needle therein.

7. The apparatus of claim 6 wherein said isolation cell is made of a material selected from the group consisting of stainless steel, nickel plated steel, copper, aluminum, and brass.

8. The apparatus of claim 7 wherein said material of said isolation cell is a material which has been surface treated.

9. The apparatus of claim 6 wherein said elongated member of said isolation cell is a hollow cylinder having a length sufficient to enclose about 20 to about 90% of the length of said needle.

10. The apparatus of claim 1 wherein said crimping means comprise:

hammer means engaged in an operational relationship with said anvil means;

energizing means for energizing said hammer means; and triggering means located at said anvil means for triggering said energizing means when said isolation cell having said tip of said needle therein is placed in said anvil means.

11. The apparatus of claim 10 wherein said hammer means comprise an elongated hammer pin positioned in slidable relationship with a hammer body such that when said hammer means are energized by said energizing means, an impacting end of said hammer pin impacts with a sufficient force against said isolation cell to deform said cell and said tip of said needle positioned therein to permanently affix said isolation cell to said tip of said needle.

12. The apparatus of claim 11 wherein said energizing means comprise an electrically driven solenoid in an operational relationship with said elongated hammer pin.

13. The apparatus of claim 11 wherein said impacting end of said hammer pin is shaped in the form of a wedge or a ball shape.

14. The apparatus of claim 1 wherein said medical device is a disposable syringe having said needle attached thereto.

15. The apparatus of claim 1 wherein said positioning means further comprise:

isolation cell dispenser means detachably engaged to a positioning block disposed on said base structure, said dispenser means defining a cavity adapted to store a plurality of said isolation cells arrayed to allow said placement of said tip inside one of said isolation cells and further adapted to allow dispensing of one of said isolation cells at a time to aperture means located on said dispenser means and situated at said positioning block for allowing said insertion through said orifice of said tip of said needle in said dispensed isolation cell and for allowing extraction from said apparatus of said dispensed isolation cell having said tip of said needle affixed thereto; and isolation cell dispenser biasing means positioned in said cavity of said isolation cell dispenser means to urge said plurality of said isolation cells towards said aperture means.

16. The apparatus of claim 15 wherein said dispenser biasing means comprise a compression spring mounted on a push rod.

17. The apparatus of claim 15 wherein said base structure is provided with dispenser alignment means to align said dispenser means with said positioning block.

18. The apparatus of claim 15 wherein said isolation cell dispenser means are provided with clip means to engage or disengage said dispenser means with said positioning block.

19. A needle-capping apparatus for a safe disposal of a used or otherwise unsanitary needle of a medical device comprising:

a base structure;

needle-alignment means disposed on said base structure, said alignment means having an orifice for inserting said needle of said medical device therethrough, said needle-alignment means further comprising a left side and a right side member where each member has substantially half of said orifice disposed thereon, said members being adapted to separate from each other during extraction from said apparatus of said needle having said isolation cell affixed thereto, and needle alignment biasing means for keeping said members close to each other during said insertion of said needle through said orifice;

isolation cell dispenser means detachably engaged to a positioning block, said positioning block being aligned in an operating relationship with said needle-alignment means, said dispenser means defining a cavity adapted to store a plurality of isolation cells arrayed to allow placement of a tip of said needle inside one of said isolation cells and further adapted to allow dispensing of one of said isolation cells at a time to aperture means located on said dispenser means and situated at said positioning block for allowing said insertion through said orifice of said tip of said needle in said dispensed isolation cell and for allowing extraction from said apparatus of said dispensed isolation cell having said tip of said needle affixed thereto;

isolation cell dispenser biasing means disposed in said cavity of said isolation cell dispenser means to urge said plurality of said isolation cells towards said aperture means;

anvil means disposed on said base structure and aligned in an operating relationship with said aperture means to allow placement of a portion of said dispensed isolation cell having said tip of said needle therein onto said anvil means; and crimping means positioned on said base structure and aligned with said anvil means and said aperture means for permanently affixing said dispensed isolation cell to said tip of said needle, said crimping means further comprising hammer means engaged in an operational relationship with said anvil means, energizing means for energizing said hammer means, and triggering means located at said anvil means for triggering said energizing means by said dispensed isolation cell having said tip of said needle therein.

20. The apparatus of claim 19 wherein said plurality of said isolation cells are hollow elongated members closed at one end and open at the opposite end.

21. The apparatus of claim 19 wherein said medical device is a disposable syringe having said needle attached thereto.

* * * * *